US008063236B2

(12) United States Patent
Veige et al.

(10) Patent No.: US 8,063,236 B2
(45) Date of Patent: Nov. 22, 2011

(54) METHOD FOR TRANSFERRING N-ATOMS FROM METAL COMPLEXES TO ORGANIC AND INORGANIC SUBSTRATES

(75) Inventors: Adam Veige, Gainesville, FL (US); Soumya Sarkar, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 295 days.

(21) Appl. No.: 12/437,845

(22) Filed: May 8, 2009

(65) Prior Publication Data

US 2009/0281343 A1 Nov. 12, 2009

Related U.S. Application Data

(60) Provisional application No. 61/051,599, filed on May 8, 2008.

(51) Int. Cl.
*C07F 11/00* (2006.01)
*C07C 253/00* (2006.01)
(52) U.S. Cl. .......................... 556/58; 558/311
(58) Field of Classification Search .................. 556/58; 558/311
See application file for complete search history.

(56) References Cited

OTHER PUBLICATIONS

Agapie, T. et al., "Cyclometalated Tantalum Diphenolate Pincer Complexes: Intramolecular C-H/M-CH$_3$ σBond Metathesis May Be Faster than O-H/M-CH$_3$ Protonolysis," *Organometallics*, 2007, pp. 2957-2959, vol. 26.
Sarkar, S. et al., "Synthesis, Characterization, and Reactivity of a d$^2$, Mo(IV) Complex Supported by a New OCO-Trianionic Pincer Ligand," *J. Am. Chem. Soc.*, 2008, pp. 1116-1117, vol. 130.
Yandulov, D.V. et al., "Catalytic Reduction of Dinitrogen to Ammonia at a Single Molybdenum Center," *Science*, Jul. 4, 2003, pp. 76-78, vol. 301.

*Primary Examiner* — Porfirio Nazario Gonzalez
(74) *Attorney, Agent, or Firm* — Saliwanchik, Lloyd & Eisenschenk

(57) ABSTRACT

A complex for transference of a nitrogen atom to an electrophilic reagent comprises a hard-hard-hard pincer ligand and an early transition metal bound to a nitride. The pincer ligand can be an OCO ligand and the transition metal can be Mo. The complex can be used to transfer the nitrogen atom bound to the metal to an electrophile in a method to produce a nitrogen containing molecule. In one novel nitrogen transfer reaction, a Mo—N triple bond is broken where the nitrogen transfers to the sp$^2$ hybridized carbon of an acid chloride to form a nitrile.

17 Claims, 4 Drawing Sheets

METHOD FOR TRANSFERRING N-ATOMS FROM METAL COMPLEXES TO ORGANIC AND INORGANIC SUBSTRATES

CROSS-REFERENCE TO RELATED APPLICATION

This application claims the benefit of U.S. Provisional Application Ser. No. 61/051,599, filed May 8, 2008, which is hereby incorporated by reference in its entirety, including any figures, tables, or drawings.

BACKGROUND OF THE INVENTION

Nitrogen fixation is a process by which nitrogen gas is converted to heteroatomic molecules such as ammonia. Nitrogen fixation is carried out biologically by nature using enzymes, particularly nitrogenase containing Mo—Fe, V—Fe and Fe metals in the enzymatic catalyst or cofactors, although the detailed chemical mechanism remains unknown. Natural fixation is estimated to result in about $2 \times 10^{11}$ kg of ammonia every year at ambient temperatures and pressures. Industrially, the chemical synthesis of about $8 \times 10^{10}$ kg per year is produced by the Haber-Bosch process, which, although catalyzed by either Fe or Ru catalyst, requires very high temperatures and pressures. Hence, efforts have been made to identify catalysts that can mimic nitrogenase enzymes and fix nitrogen at near ambient conditions.

Although a few bimetallic catalysts have demonstrated activation of nitrogen, no catalytic bimetallic system has been identified. A monometallic catalyst has been identified, Yandulov et al. *Science*, 2003, 76, 301, that uses a tetradentate ligand with the early transition metal Mo where a turnover number of four has been observed. This catalyst is perceived as being active due to the ability of the ligand to inhibit formation of bimetallic complexes, to sterically protect the coordination site as a monometallic species, and increase the solubility of intermediates in nonpolar solvents. Hence, design of ligands and there use in organometallic compounds that promote stable nitrides of Mo or other similar transition metals may result in compounds for nitrogen fixation.

Pincer ligands are chelating agent that binds metals tightly to three adjacent coplanar sites. The pincer-metal interaction is very rigid and typically confers a high thermal stability to the ligand metal complexes. Organic portions and substituents define a hydrophobic pocket around the coordination site. These ligands traditionally share the common feature of an aromatic central aromatic unit. To this central unit are attached, in the ortho positions, two arms whose electronic and steric properties can be varied in many different ways. The ability to vary the properties of pincer ligands has been exploited for numerous complexes to be used as catalysis. Early work mainly focused on ligands where the central binding site is carbon and the peripheral binding sites are phosphorous, generally referred to by the atomic symbols of the donor atoms at the binding sites as the PCP systems. More recently CCC, CNC, CNS, NNN, NCN, PNP, OCO, SCS, SNS have been reported. Most frequently the pincer ligand transition metal complexes have been those of group VII-X metals where low coordinate and low oxidation state prevail and the metals are tolerant of a wide variety of substituents.

Early transition metal (group III-VI) pincer complexes are significantly less common and typically display high oxidation states and high coordination numbers, are typically electrophilic, and are intolerant of many functional groups. As most presently known pincer ligands have multiple soft donor atoms for metal binding, the ligands are not well suited to forming complexes with the early transition metals. Those that have been prepared include: pincer dicarbene complexes of CNC ligands with V, Ti, Cr, Mn, and Nb; non traditional NNN ligands with Zr; NCN ligands with W, Mo, Ti, La, Ta and Mn; and OCO ligands with Ti and Ta. The early transition metal form complexes with Pincer type ligands where the donors are all considered hard donors. As early transition metals, such as Mo, have been identified as promising for nitrogen fixation catalysts when sufficiently stable and bulky polydentate ligands are present, pincer complexes that can undergo nitrogen atom transfer from a complex are desired.

BRIEF SUMMARY OF THE INVENTION

An embodiment of the invention is directed to a complex where a hard-hard-hard pincer ligand is bound to an early transition metal, which has a bond to a nitride. The pincer ligand can be an OCO pincer ligand such as

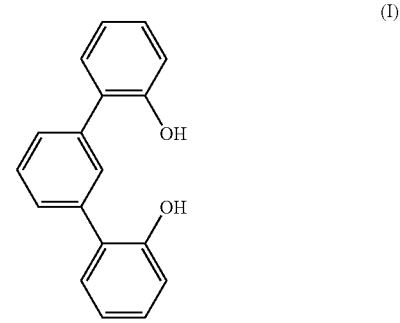

(I)

where all carbons at positions 3,4,5,4',5',6',3",4" and 5" can be substituted with an alkyl or other substituent that is unreactive toward the metal and the metal nitride of the complex. A useful metal is Mo, which can be bonded to the nitrogen by a triple bond. One embodiment of the complex is

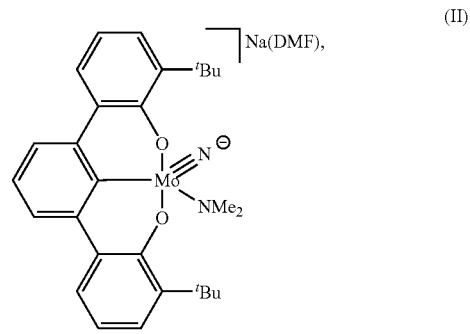

(II)

which is an anionic complex that contains t-butyl groups at the 3 and 3" positions.

Another embodiment of the invention is a method to employ the pincer complex to convert an electrophilic compound into a nitrogen comprising molecule. The pincer complex described above and an electrophilic reagent are mixed under mild conditions, typically in solution such that a nitrogen transfer occurs between the complex and reagent to form the nitrogen comprising molecule. In one embodiment of the method the electrophilic reagent is an acid chloride to which the complex transfers nitrogen to form a nitrile. Trimethylacetyl chloride can be used for the novel transformation of an acid chloride to a nitrile such that trimethylacetonitrile is formed under mild conditions.

DETAILED DESCRIPTION OF THE INVENTION

One embodiment of the invention is directed to a metallic nitride pincer ligand complex that can be used for the formation of nitrogen comprising compounds. The pincer ligand is of a hard-hard-hard type, where three donor atoms for complexation are of a hard type as known to those skilled in the art. The metallic species of the complex is an early transition metal (group 3-6) in a high oxidation state. In one embodiment, the transition metal is molybdenum (Mo). The nitride of the complex is in a form that can readily add to an electrophile and after addition of the electrophile, a nitrogen containing compound can be released from the complex. Another embodiment of the invention is a method for the synthesis of a nitrogen compound employing the transfer of nitrogen from an early transition metal nitride pincer ligand complex.

The novel complex is derived from an OCO pincer ligand of the structure:

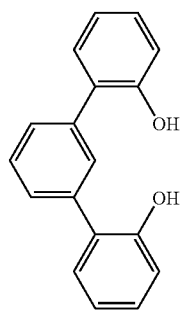

(I)

where all carbons at positions 3,4,5,4',5',6',3",4" and 5" can be substituted, for example, with an alkyl groups such as methyl, ethyl, n-propyl, i-propyl, n-butyl, i-butyl t-butyl, or larger alkyl group or any other substituent that does not inhibit a desired transformation of the metal-nitrogen bond to be formed in the pincer complex. The metal can be any transition metal from group 3-6 and is preferably Mo(VI). Other ligands can be attached, such as amido, alkyl amido, dialkylamido and halo.

In one embodiment of the invention, the metallic nitride pincer ligand complex has the structure:

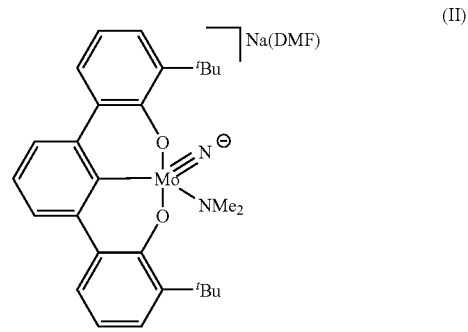

(II)

where steric hindrance is provided by the OCO ligand with t-butyl groups in the 3 and 3" positions.

The metallic nitride pincer ligand complex II is capable of undergoing reaction with an electrophile. Complex II can be protonated to yield:

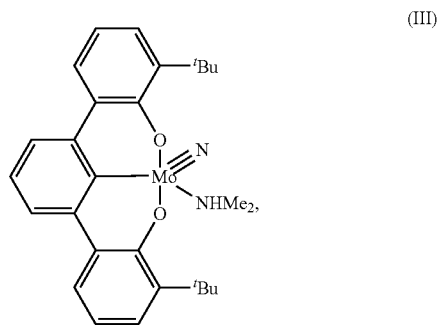

(III)

where the C—Mo bond is retained. In another reaction with an electrophile, complex II can be combined with trimethylchlorosilane in THF to yield the addition product:

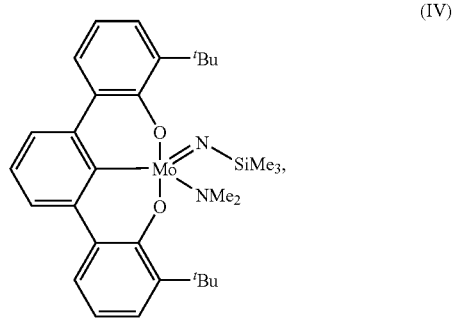

(IV)

where the electrophile has undergone the unprecedented addition to a metal nitride triple bond. The addition to the metal nitride triple bond also occurs with other electrophiles such as iodomethane in a very low dielectric solvent such as benzene, such that complex II yields:

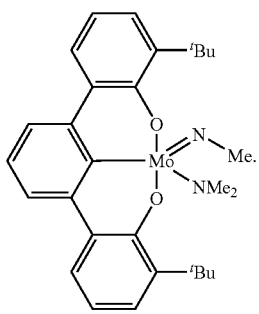

(V)

In addition to electrophilic addition, substitution reactions with nitrogen fixation can occur. For example, complex II readily reacts with trimethylacetyl chloride where nitrogen transfer to the carbonyl carbon results in the formation to trimethylacetonitrile with transfer of the oxygen of the carbonyl to the complex to form:

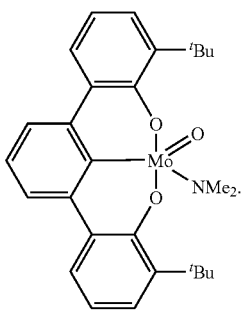

(VI)

MATERIALS AND METHODS

The O—H and C—H bond activation to metalate OCO ligand,

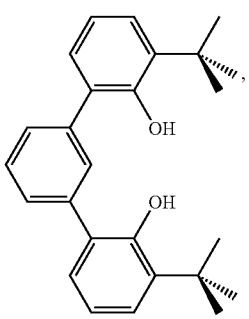

(VII)

is achieved under mild conditions where Mo(IV), d² ($\mu_{eff}$ 3.06$\mu_B$) amido-dimethylamine complex, [3,3''-di-tert-butyl-2,2''-di-(hydroxy-κO)-1,1':3',1''-terphenyl-2'-yl-κC²'](N-methylmethanaminato) bis(N-methylmethanamine)molybdenum(IV),

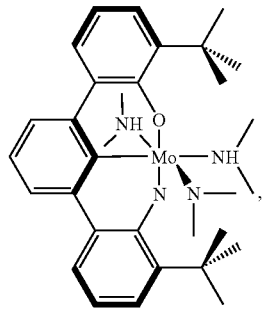

Figure 1:
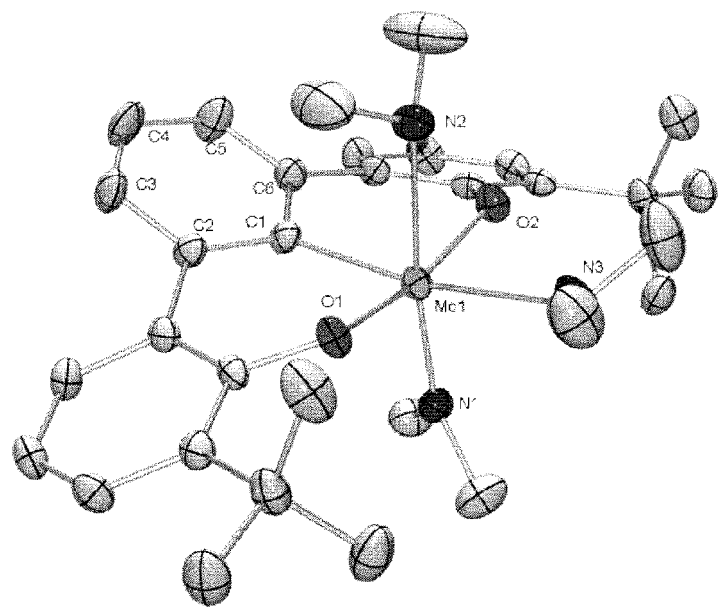
FIG. 1 is an ORTEP molecular structure of Complex VIII as determined by X-ray structural analysis.

(VIII)

is formed at −35° C. upon combining pentane solutions of VII and Mo(NMe$_2$)$_4$. Complex VIII precipitates in 80% yield as an orange powder and can be recrystallization from 1,2-dimethoxyethane (DME) at −35° C. The $^1$H NMR spectrum of paramagnetic VIII revealed broad resonances that exhibited signals for t-butyl protons at 2.83 ppm, NHMe$_2$ protons at 2.01 ppm, and three sets of aryl-H resonances, where one set appears extremely downfield at 66.7 ppm, one set appears at 9.74 ppm and one set appears upfield at −9.85 ppm. X-ray structural analysis on a single crystal obtained from a cooled concentrated DME solution of VIII is shown in FIG. 1. FIG. 1 clearly displays the trianionic tridentate pincer ligand with an octahedral Mo(IV) center bound to the pincer ligand, two pyramidal dimethylamines (d(Mo1-N2)) 2.390(3) Å, d(Mo—N3)) 2.430(3) Å) and one trigonal dimethylamido (d(Mo—N1)) 1.928 (3) Å). The dimethylamido ligand is twisted away from the N2-Mo—N3 plane by 35°, breaking an otherwise perfect solid-state Cs symmetry. Considerable strain is imparted to the pincer backbone and is attributable to congestion caused by the dimethylamine ligand trans to C1. The N-Me groups are nearly parallel to the O1-C1-O2 plane, which forces them into the t-butyls of the pincer ligand and imposes strain as indicated by the 33° and 32° torsion angles observed between the peripheral aryl connections, with the central ring being upwardly bent by 30°.

Figure 2:
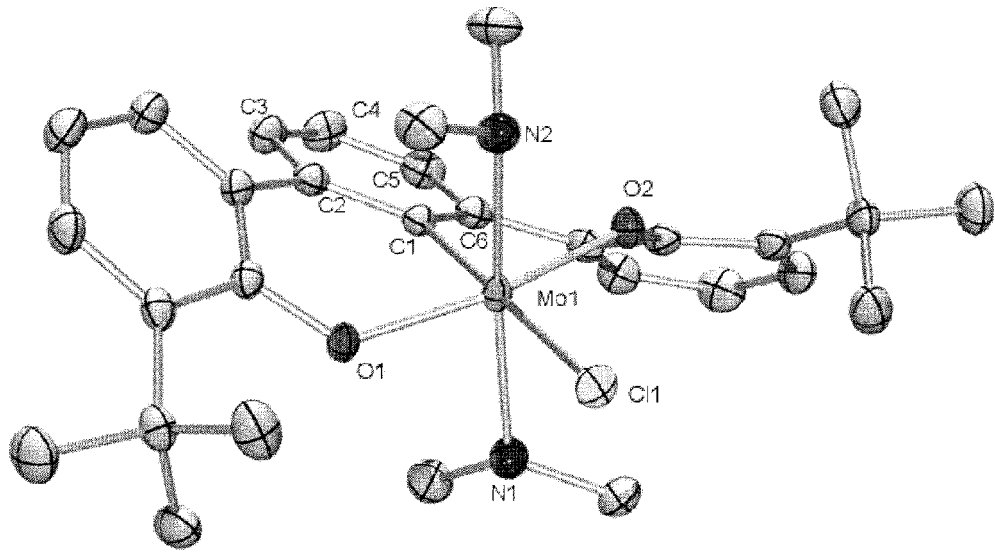
FIG. 2 is an ORTEP molecular structure of Complex 1× as determined by X-ray structural analysis.

When benzene solutions of VIII are treated with 2,6-lutidine-HCl and left without agitation, large purple-red crystals deposit within 2 hours. A $^1$H NMR spectrum of the crystals revealed aryl-H resonances downfield at 28.81 ppm ($v^{1/2}$=12 Hz) and upfield resonance at −1.10, −1.98, and −5.34 ppm ($v^{1/2}$=7 Hz). The N-Me protons are broad and located at −2.18 ppm ($v^{1/2}$=153 Hz). By single-crystal X-ray diffraction analysis, as shown in FIG. 2, the crystals were identified as the d2 ($v_{eff}$=2.56$\mu_B$) Mo(IV) chloride complex,

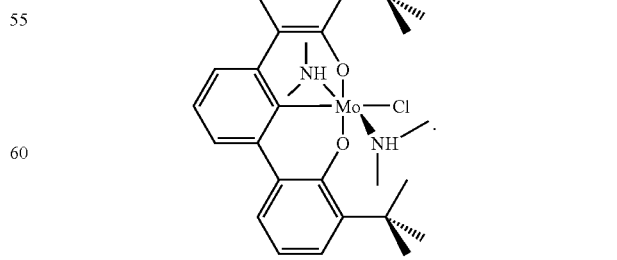

(IX)

The octahedral Mo(IV) center is coordinated by the pincer ligand, trans-dimethylamines, and a chloride. In contrast to VIII, IX displays C2 symmetry from a 33° twist in the backbone along the Cl1-Mo—Cl axis, due to the smaller size of the Cl ligand. The dimethylamine ligands orient off axis by 57° and are rotated 88° with respect to each other, which again can be attributed to steric interactions.

The dimethylamines on IX are bound tightly and do not release under vacuum nor substitute with THF, DME, or CO, even at elevated temperatures (80° C.). Attempts to reduce IX with Na/Hg or to alkylate with MeMgCl were unsuccessful. Complex IX does not react with Me₃SiN₃ or NaN₃ in refluxing THF. However, when the more polar solvent DMF is used, red solutions of IX in DMF turn yellow-orange when treated with NaN₃ at 25° C. and releases $N_2$ to provide a mixture of products that are inseparable. A single crystal of one species was procured from a mixture of solids and identified as the non-pincer yellow Mo(VI) nitride complex:

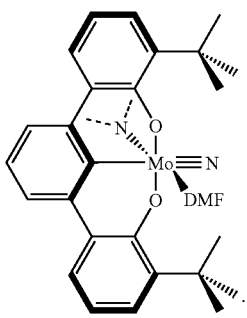

(X)

Figure 3:
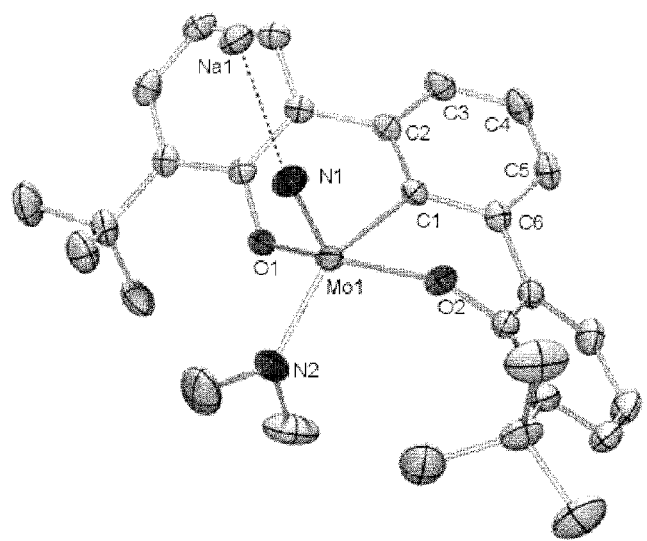
FIG. 3 is an ORTEP molecular structure of Complex II as determined by X-ray structural analysis with DMF molecules removed from the structure for clarity.
Figure 4:
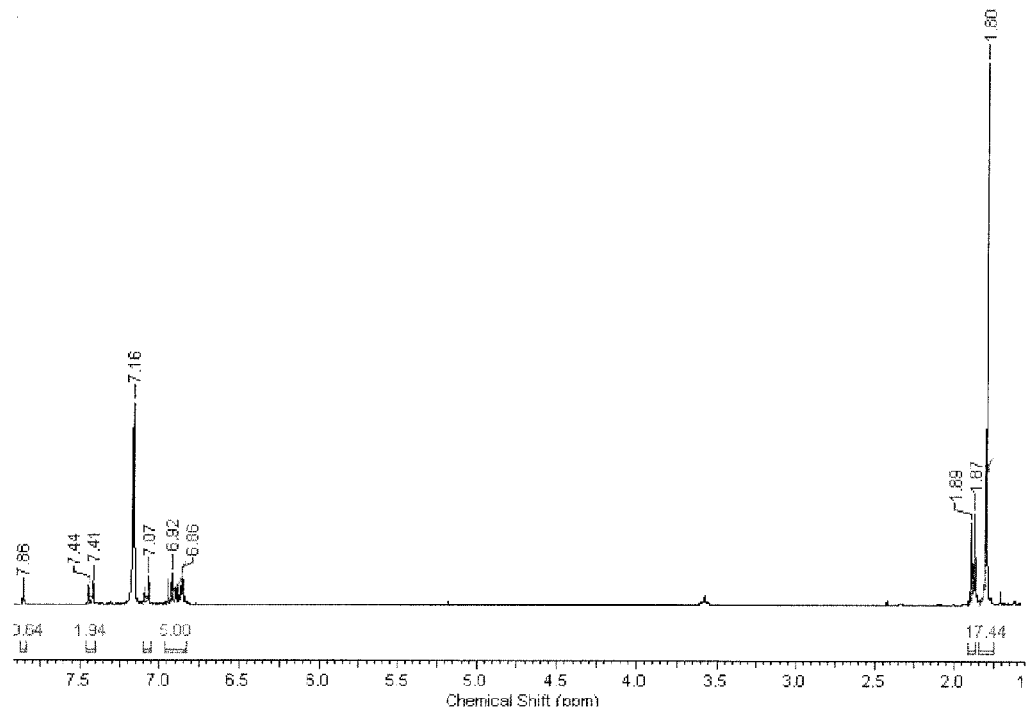
FIG. 4 is a $^1$H NMR spectrum of Complex III in $C_6D_6$.

Treating VIII with NaN₃ in DMF produced II as a dimer in excellent yield (86%) and purity. The molecular structure by X-ray analysis is shown in FIG. 3. The nitride occupies the apical position of a distorted square pyramid (d(Mo≡N)= 1.6601(15) Å), but unlike complex X, the OCO ligand is attached as a trianionic pincer. To balance charge, a Na ion, solvated with DMF, is present 2.4453(17) Å from the nitride. FIG. 4 displays a $^1$H NMR spectrum of II in $C_6D_6$ that is consistent with the X-ray structure.

By treating complex II with 2,6-lutidine-HCl in THF, where addition is made at −35° C. and allowed to warm to room temperature, neutral complex III forms, as reflected in the $^1$H NMR spectrum, shown in FIG. 4. Protonation of complex II occurs at the amido nitrogen to yield the N-methylmethylaminato ligand.

Figure 5:
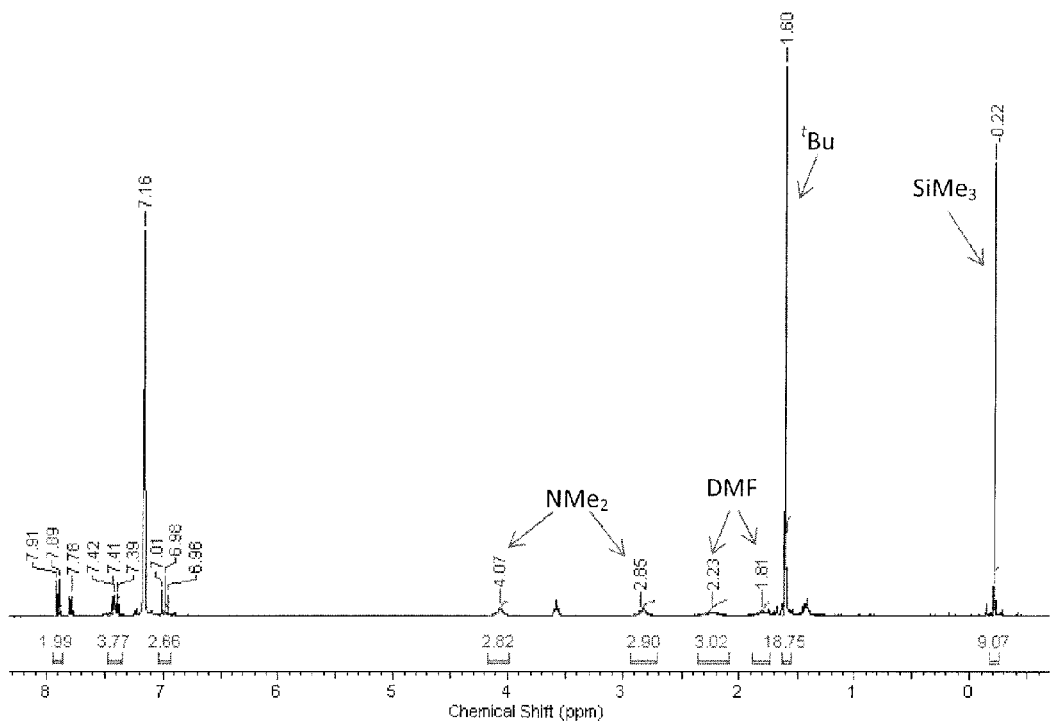
FIG. 5 is a $^1$H NMR spectrum of Complex IV in $C_6D_6$.
Figure 6:
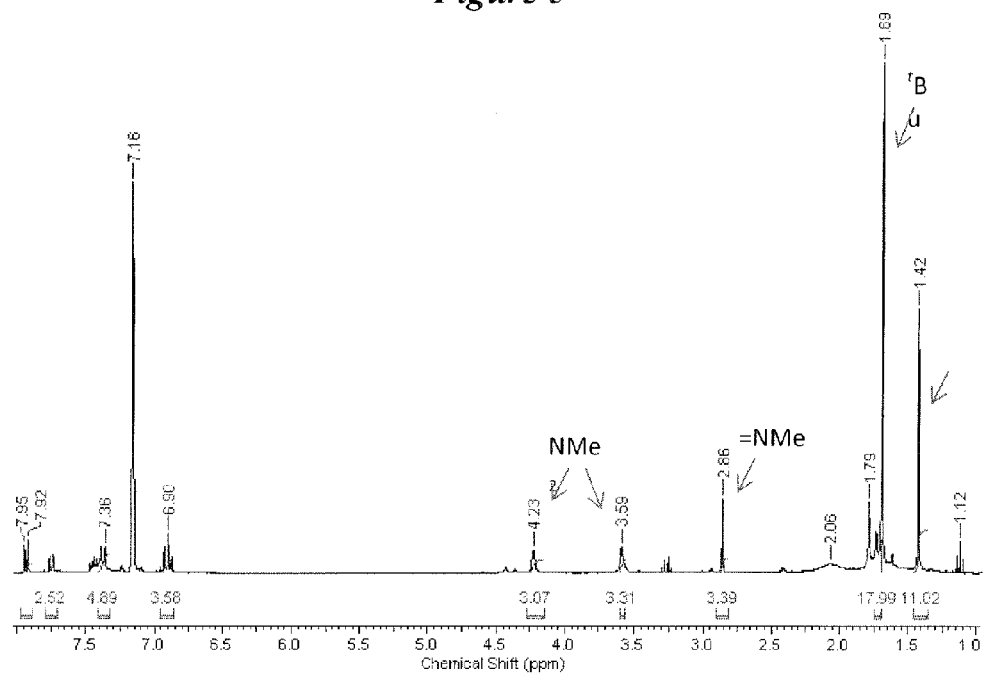
FIG. 6 is a $^1$H NMR spectrum of Complex V in $C_6D_6$.

It was found that by treating complex II with trimethylehlorosilane in THF, a facile addition of the electrophilic TMS cation to the Mo≡N triple bond occurs to form Complex IV, as reflected in the $^1$H NMR spectrum shown in FIG. 5. In like manner, treating complex II with iodomethane in benzene resulted in the addition of the electrophilic methyl group to the Mo≡N triple bond to form complex V when warmed to 60° C. for 20 hours. The $^1$H NMR spectrum of V is shown in FIG. 6.

Figure 7:
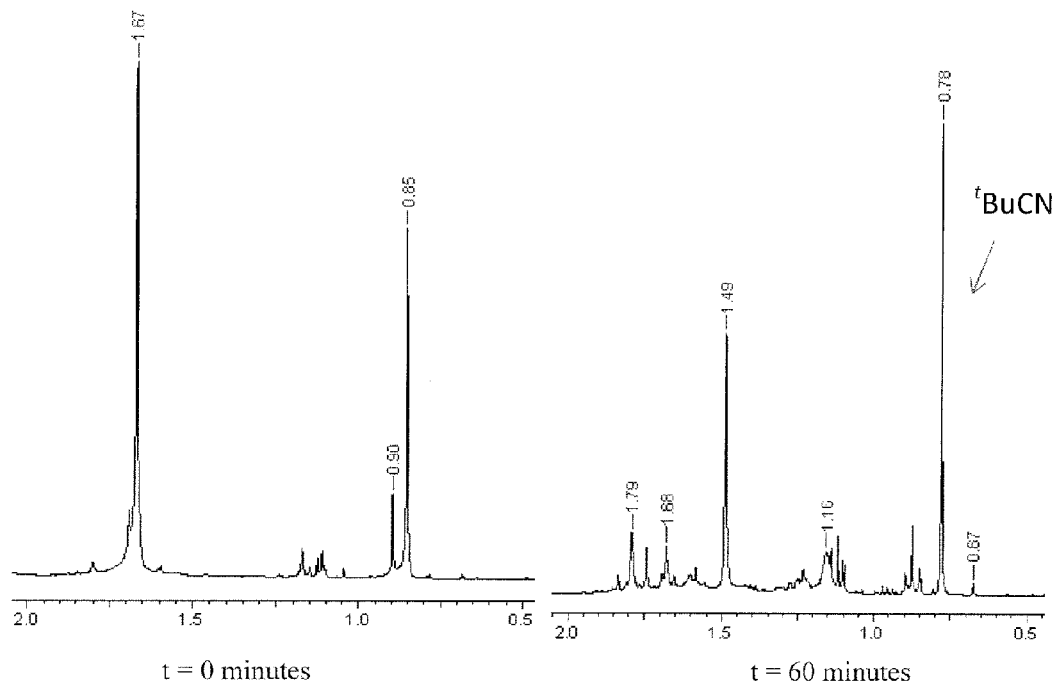
FIG. 7 is a composite of $^1$H NMR spectrum of Complex II and trimethylacetyl chloride which is converted to primarily Complex VI, trimethylacetonitrile and NaCl in $C_6D_6$ after 60 minutes.

Treating complex II with trimethylacetyl chloride resulted in the Mo≡O complex VI where the nitrogen atom transferred to the carbonyl carbon of the acid chloride to form trimethylacetonitrile. The transformation was carried out in benzene at 50° C. where the conversion was clearly seen by the appearance of the sharp signal for trimethylacetonitrile at 0.78 ppm in the $^1$H NMR spectrum, as shown in FIG. 7.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A complex comprising a hard-hard-hard pincer ligand, an early transition metal and a nitride bound to said metal.

2. The complex of claim 1, wherein said pincer ligand is an OCO pincer ligand.

3. The complex of claim 2, wherein said OCO pincer ligand is derived from:

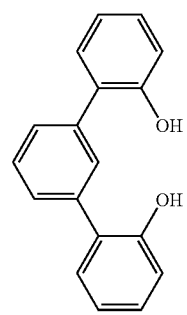

(I)

where all carbons at positions 3,4,5,4',5'6',3",4" and 5" can be substituted with an alkyl or other substituent that is unreactive toward said metal and said nitride.

4. The complex of claim 1, wherein said metal comprises Mo.

5. The complex of claim 1, wherein said nitride is bonded to said metal by a triple bond.

6. The complex of claim 1, wherein said complex has the structure:

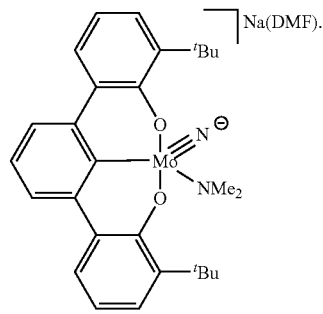

(II)

7. A method of forming a nitrogen comprising molecule comprising the steps of:
   providing a complex comprising a hard-hard-hard pincer ligand, an early transition metal and a nitride bound to said metal;
   providing an electrophilic reagent;

mixing said electrophilic reagent with said complex, wherein said complex transfers the nitrogen of said nitride to said electrophilic reagent; and isolating said nitrogen comprising molecule.

8. The method of claim 7, wherein said pincer ligand is an OCO pincer ligand.

9. The method of claim 7, wherein said OCO pincer ligand is derived from:

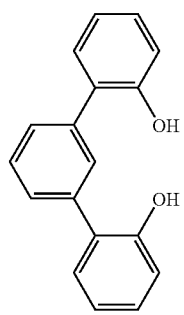

(I)

where all carbons at positions 3,4,5,4',5',6',3",4" and 5" can be substituted with an alkyl or other substituent that is unreactive toward said metal and said nitride.

10. The method of claim 7, wherein said metal comprises Mo.

11. The method of claim 7, wherein said nitride is bonded to said metal by a triple bond.

12. The method of claim 7, wherein said complex comprises:

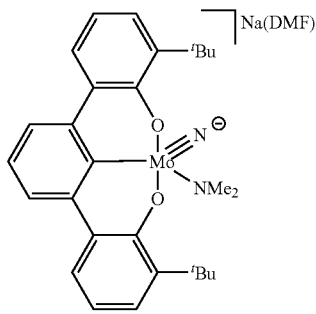

(II)

13. The method of claim 7, wherein said step of providing a complex comprises said complex in a solvent.

14. The method of claim 7, wherein said step of providing an electrophilic reagent comprises said reagent in a solvent.

15. The method of claim 7, wherein said electrophilic reagent comprises an acid chloride and said nitrogen comprising compound comprises a nitrile.

16. The method of claim 15, wherein said acid chloride comprises trimethylacetyl chloride.

17. The method of claim 7, wherein said complex comprises II, said electrophilic reagent comprises trimethylacetyl chloride, and said nitrogen comprising molecule comprises trimethylacetonitrile.

* * * * *

UNITED STATES PATENT AND TRADEMARK OFFICE
CERTIFICATE OF CORRECTION

PATENT NO. : 8,063,236 B2
APPLICATION NO. : 12/437845
DATED : November 22, 2011
INVENTOR(S) : Adam Veige and Soumya Sarkar Page 1 of 1

It is certified that error appears in the above-identified patent and that said Letters Patent is hereby corrected as shown below:

Column 3,
Line 9, "Complex 1x" should read --Complex IX--.

Column 6,
Line 28, "Mo(TV)" should read --Mo(IV)--.
Line 49, "($\upsilon_{eff}$ = 2.56 $\mu_B$)" should read --($\mu_{eff}$ = 2.56 $\mu_B$)--.

Column 7,
Line 44, "lutidine-HCl" should read --lutidine-HCl--.
Lines 50-51, "trimethylehlorosilane" should read --trimethylchlorosilane--.

Signed and Sealed this
Thirteenth Day of March, 2012

David J. Kappos
*Director of the United States Patent and Trademark Office*